United States Patent
Han et al.

(10) Patent No.: US 9,968,712 B1
(45) Date of Patent: May 15, 2018

(54) ORGANIC/INORGANIC HYBRID-BIODEGRADABLE POROUS POLYMER SCAFFOLDS AND PREPARATION METHOD THEREOF

(71) Applicant: Korea Institute of Science and Technology, Seoul (KR)

(72) Inventors: Dong Keun Han, Seoul (KR); Yoon Ki Joung, Seoul (KR); Eugene Lih, Seoul (KR); Yun Ah Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days. days.

(21) Appl. No.: 15/377,372

(22) Filed: Dec. 13, 2016

(30) Foreign Application Priority Data

Oct. 31, 2016 (KR) ........................ 10-2016-0143469

(51) Int. Cl.
| | |
|---|---|
| *A61K 9/00* | (2006.01) |
| *A61L 27/58* | (2006.01) |
| *A61L 27/56* | (2006.01) |
| *A61L 27/10* | (2006.01) |
| *A61L 27/54* | (2006.01) |
| *A61L 27/34* | (2006.01) |
| *A61L 27/18* | (2006.01) |
| *A61L 27/36* | (2006.01) |
| *A61L 27/26* | (2006.01) |
| *C12N 5/00* | (2006.01) |

(52) U.S. Cl.
CPC ............ *A61L 27/58* (2013.01); *A61K 9/0024* (2013.01); *A61L 27/10* (2013.01); *A61L 27/18* (2013.01); *A61L 27/26* (2013.01); *A61L 27/34* (2013.01); *A61L 27/3633* (2013.01); *A61L 27/54* (2013.01); *A61L 27/56* (2013.01); *C12N 5/0068* (2013.01); *A61L 2300/252* (2013.01); *A61L 2300/412* (2013.01); *A61L 2300/414* (2013.01); *A61L 2400/18* (2013.01); *C12N 2533/90* (2013.01)

(58) Field of Classification Search
CPC .................................................... A61K 9/0024
See application file for complete search history.

(56) References Cited

FOREIGN PATENT DOCUMENTS

| KR | 10-2010-0041027 A | 4/2010 |
|---|---|---|
| KR | 10-2011-0077244 A | 7/2011 |
| KR | 10-2012-0029130 A | 3/2012 |

*Primary Examiner* — Carlos A Azpuru
(74) *Attorney, Agent, or Firm* — NSIP Law

(57) ABSTRACT

Provided is an organic/inorganic hybrid-porous biodegradable polymer scaffold, which includes basic ceramic nanoparticles, an animal tissue or cell-derived bioactive first extracellular matrix material, and a biodegradable polymer and in which inner walls of pores are coated with a second extracellular matrix material.

17 Claims, No Drawings

ORGANIC/INORGANIC HYBRID-BIODEGRADABLE POROUS POLYMER SCAFFOLDS AND PREPARATION METHOD THEREOF

CROSS-REFERENCE TO RELATED APPLICATIONS

This application claims the benefit under 35 USC 119(a) of Korean Patent Application No. 10-2016-0143469, filed on Oct. 31, 2016, in the Korean Intellectual Property Office, the entire disclose of which is incorporated herein by reference for all purposes.

BACKGROUND

1. Field of the Invention

The present invention relates to an organic/inorganic hybrid-porous biodegradable polymer scaffold prepared by having ceramic nanoparticles having excellent bioactivity and mechanical properties and an extracellular matrix material bulk-mixed with a biodegradable polymer and coating the mixture on the scaffold surface and a method for preparing the same, and more particularly, to a hybrid scaffold for tissue regeneration, in which a biodegradable polymer scaffold includes basic ceramic nanoparticles having a high dispersion property and high stability and a bioactive material derived from the extracellular matrix of a target tissue, and a porous surface is coated with an extracellular matrix-based material to inhibit inflammatory response due to a biomedical implant, improve mechanical properties, and have a highly efficient tissue regeneration capability, use thereof, and a method for preparing the same.

2. Discussion of Related Art

Tissue engineering, one of the new fields emerged with the development of science, is an applied study for understanding the relationship between structure and function of biological tissue according to an interdisciplinary study between basic concepts of bioscience, engineering and medical science, and scientific technologies, and further, for maintaining, improving or restoring functions of a human body using artificial tissue capable of being implanted in the body to replace or regenerate damaged tissue or organ with normal tissue.

A representative tissue engineering technique is summarized as follows; First, a targeted tissue is taken from a patient's body, and cells are isolated from the tissue graft and proliferated as much as necessary by culturing the isolated cells. The proliferated cells are in vivo cultured for a certain time by seeding the proliferated cells in a porous biodegradable polymer scaffold, thereby obtaining a hybrid cell-polymer complex, and the complex is implanted into the body again. The present invention employs the technique of supplying oxygen and nutrients to implanted cells by diffusion of a body fluid until angiogenesis occurs in most types of tissue or organs, creating new tissue and organ through proliferation and differentiation of cells when blood vessels in the body are grown, thus resulting in supplying blood, and meanwhile losing the polymer scaffold through degradation.

For such a tissue engineering study, first, it is important to prepare a biodegradable polymer scaffold that is similar to biological tissue. The main requirements for a scaffolding material used in regeneration of human tissue are for sufficiently playing a cytophilic role by adhering tissue cells to a surface of the material to form tissue with a three-dimensional structure and playing a role of an intermediate barrier located between implanted cells and host cells. This means that the scaffolding material needs to have non-toxic biocompatibility, without inducing blood coagulation or inflammatory response after implantation.

Also, a biodegradable polymer that degrades as soon as new tissue is formed and ultimately does not leave foreign materials in the body is an attractive candidate for a scaffolding material. Presently, widely used biodegradable polymers include poly(glycolic acid) (PGA), poly(lactic acid) (PLA), polylactic acid-glycolic acid copolymer (PLGA), poly-ε-caprolactone (PCL), polyamino acid, polyanhydride, polyorthoester, and a copolymer thereof. However, up to the present, only PGA, PLA, and PLGA have been approved by the US FDA as biodegradable polymers capable of being used in a human body and are used as porous polymer scaffolding materials for in vivo regeneration of human tissue.

Generally, biodegradable polymers are widely used for biomedical implants since they are completely degraded in the body after a certain time period. However, such biodegradable polymers have relatively poor physical properties in compared to other general-purpose polymers and generate acidic materials such as lactic acid, glycolic acid, hydroxycaproic acid, maleic acid, phosphazene, hydroxybutyric acid, ethoxyacetic hydroxide, sebacic acid, alcohol, trimethylene glycol, amino acid, formalin, and alkylcyanoacrylate through biodegradation, thereby causing inflammatory response and cytotoxicity in the human body.

To eliminate such disadvantages, a technique for neutralizing acidic materials generated during degradation of a biodegradable polymer with basic ceramic nanoparticles to completely inhibit the production of acidic materials (Korean Patent Application No. 10-2010-0091028) is disclosed. Also, in a method of completely inhibiting the production of an acidic material by adding basic ceramic nanoparticles in a biodegradable polymer, a method is disclosed, for turning basic ceramic particles into nanosized particles to improve neutralization efficiency, mechanical properties, application to biomedical implants, and usability in storage (Korean Unexamined Patent Application Publication No. 10-2012-0029130).

Also, to overcome the limitations in biocompatibility and tissue regeneration capability of the synthetic polymer material as a biomedical implant, recently, development of a scaffold for tissue regeneration using a natural polymer and an extracellular matrix has been suggested by several researchers (for example, Korean Unexamined Patent Application Publication No. 10-2010-0041027), but the scaffold lacks good physical and mechanical properties, has a difficulty with controlling degradation duration, has a limitation in chemical modification due to low solubility in an organic solvent, and cannot be applied in various forms.

Also, various methods, such as physicochemical modification and plasma treatment and introduction of a hydrophilic polymer, have been suggested as a method for hydrophilizing a biodegradable polymer porous scaffold to facilitate cell penetration and adhesion of a polymer scaffold and cell migration after implantation into the body, to facilitate cell culture in the scaffold by facilitating the supply of oxygen and nutrients, and to usefully utilize a scaffold for tissue engineering by stimulating cell growth, and, as a method for improving cell affinity of the polymer scaffold, various methods have been attempted for coating a porous surface of the scaffold with a material derived from an extracellular matrix. However, these methods are complicated and time-consuming and have limitations in unintentionally changing properties such as changing a specific physical property in the case of a polymer having a low molecular weight and reducing a pore size after surface coating scaffold pores, in particular.

SUMMARY OF THE INVENTION

To overcome the limitations of the conventional art described above, the present invention is directed to providing a highly functional hybrid scaffold, which serves as a polymer scaffold constituting a main matrix whose pore size and density, and porosity may be adjusted, as a polymer scaffold containing prepared basic ceramic nanoparticles and an extracellular matrix material with adjustable shapes and sizes, and as a biodegradable polymer scaffold that contains basic ceramic nanoparticles and an extracellular matrix material at various concentrations and has pores coated with an extracellular matrix-based material including a decellularized extracellular matrix, thereby controlling inflammatory response inhibiting capability, cell adhesion capability, tissue regeneration capability, hydrophilicity, mechanical strength and degradation duration.

Also, the present invention is directed to providing a method for simply and efficiently preparing an organic/inorganic hybrid scaffold, which may compensate for disadvantages of conventional pure synthetic and natural polymer scaffolds, that is, in the case of synthetic polymer scaffolds, lower biocompatibility that can be more beneficial to tissue regeneration, inflammatory response of cells and tissue induced by acidic degradation products generated during degradation in the body, and difficulty in giving hydrophilicity to the polymer that is advantageous for cell penetration and exchange of oxygen, nutrients, and metabolites, and in the case of natural polymer scaffolds, while satisfying the biocompatibility requirement for tissue regeneration, having low mechanical strength and difficulty in controlling degradation duration, and may effectively induce tissue regeneration.

The objects of the present invention described above will be achieved by the constitution of the present invention as follows:

(1) An organic/inorganic hybrid-porous biodegradable polymer scaffold, which includes basic ceramic nanoparticles, an animal tissue or cell-derived bioactive first extracellular matrix material and a biodegradable polymer, and has pore inner walls coated with a second extracellular matrix material;

(2) In the organic/inorganic hybrid-porous biodegradable polymer scaffold, the second extracellular matrix material is one or more selected from the group consisting of collagen, gelatin, elastin, silk, keratin, fibrinogen, hyaluronic acid, alginate, dextran, chondroitin sulfate, heparan sulfate, keratan sulfate, dextran sulfate, a protein based on an extracellular matrix including fibronectin, laminin, polysaccharides and a glycoprotein group;

(3) In the organic/inorganic hybrid-porous biodegradable polymer scaffold, the second extracellular matrix material is an extracellular matrix from which one or more selected from the group consisting of fibroblast, vascular endothelial cells, epithelial cells, cartilage cells, osteoblasts, smooth muscle cells, cardiomyocyte, liver cells, nerve cells, intervertebral disc cells, vascular endothelial cells, vascular endothelial progenitor cells, renal progenitor cells, pancreatic progenitor cells, neural progenitor cells, cardiac progenitor cells, adipose-derived stem cells, bone marrow-derived stem cells, mesenchymal stem cells, induced pluripotent stem cells and embryonic stem cells is decellularized;

(4) In the organic/inorganic hybrid-porous biodegradable polymer scaffold, the basic ceramic nanoparticles are one or more types of metal particles selected from alkali metals and alkali earth metals, or one or more types of particles selected from the group consisting of a hydroxide of an alkali metal, an oxide of an alkali metal, a hydroxide of an alkali earth metal and an oxide of an alkali earth metal;

(5) In the organic/inorganic hybrid-porous biodegradable polymer scaffold, the alkali metal or alkali earth metal is lithium (Li), beryllium (Be), sodium (Na), magnesium (Mg), potassium (K), calcium (Ca), rubidium (Rb), strontium (Sr), barium (Ba), cesium (Cs), francium (Fr) or radium (Ra);

(6) In the organic/inorganic hybrid-porous biodegradable polymer scaffold, the oxide of an alkali metal or an alkali earth metal, the hydroxide of an alkali metal or an alkali earth metal or the compound containing an alkali metal is one or more selected from the group consisting of lithium hydroxide, beryllium hydroxide, sodium hydroxide, magnesium hydroxide, potassium hydroxide, calcium hydroxide, rubidium hydroxide, strontium hydroxide, barium hydroxide, cesium hydroxide, francium hydroxide, radium hydroxide, magnesium oxide, sodium oxide, lithium oxide, manganese oxide, potassium oxide, calcium oxide, barium oxide, cesium oxide, radium oxide, magnesium sulfoxide, magnesium chloride, magnesium carbonate, magnesium bromide, magnesium stearate, magnesium perchlorate, magnesium citrate, magnesium phosphate, magnesium nitrate, magnesium nitride, magnesium iodide, magnesium acetate, magnesium ethoxide, magnesium fluoride, magnesium hydride, manganese monoperoxyphthalate, boron magnesium hydroxide, magnesium silicide, magnesium boride, magnesium aluminate, magnesium methylate, magnesium methalocyanin, magnesium salicylate, magnesium hexafluorosilicate, struvite, huntite, whitlockite, bredigite, dolomite, calcium carbonate, fluorspar, tricalcium phosphate and hydroxyapatite;

(7) In the organic/inorganic hybrid-porous biodegradable polymer scaffold, the basic ceramic nanoparticles are surface-modied with one or more fatty acids selected from the group consisting of caprylic acid, capric acid, lauric acid, myristoleic acid, palmitoleic acid, sapienic acid, oleic acid, elaidic acid, vaccenic acid, linoleic acid, ricinoleic acid, linoelaidic acid, α-linoleic acid, arachidonic acid, eicosapentaenoic acid, erucic acid, palmitate, stearic acid, DHA, octadecanoic acid, coconut oil, palm oil, cotton seed oil, wheat germ oil, bean oil, olive oil, corn oil, sunflower oil, safflower oil, hampseed oil and canola oil;

(8) In the organic/inorganic hybrid-porous biodegradable polymer scaffold, the basic ceramic nanoparticles are one or more monomers selected from the group consisting of L-lactide, D-lactide, D,L-lactide, glycolide, caprolactone, dioxanone, trimethylene carbonate, hydroxyalkanoate, peptide, cyanoacrylate, lactic acid, glycolic acid, hydroxycaproic acid, maleic acid, phosphazene, amino acid, hydroxybutyric acid, sebacic acid, hydroxyethoxyacetic acid and trimethylene glycol, which are surface-modified with one or more polymers selected from the group consisting of poly-L-lactide, poly-D-lactide, poly-D,L-lactide, polyglycolide, polycaprolactone, poly-L-lactide-co-glycolide, poly-D-lactide-co-glycolide, poly-D,L-lactide-co-glycolide, poly-L-lactide-co-caprolactone, poly-D-lactide-co-caprolactone, poly-D,L-lactide-co-caprolactone, poly(glycolide-co-caprolactone), polydioxanone, polytrimethylene carbonate, poly(glycolide-co-dioxanone), polyamideester, polypeptide, polyorthoester, polymaleic acid, polyphosphazene, polyanhydride, polycebacicanhydride, polyhydroxyalkanoate, polyhydroxybutylate and polycyanoacrylate;

(9) In the organic/inorganic hybrid-porous biodegradable polymer scaffold, the biodegradable polymer is selected from the group consisting of polylactide, polyglycolide, polycaprolactone, polylactide-co-glycolide, polylactide-co-caprolactone, poly(glycolide-co-caprolactone), polydioxanone, polytrimethylene carbonate, poly(glycolide-co-dioxanone), polyamideester, polypeptide, polyorthoester, polymaleic acid, polyanhydride, polycebacicanhydride, polyhydroxyalkanoate, polyhydroxybutylate and polycyanoacrylate;

(10) In the organic/inorganic hybrid-porous biodegradable polymer scaffold, the animal tissue or cell-derived bioactive first extracellular matrix material is one or more selected from the group consisting of a group having a fiber structure, an osteogenic differentiation and ossification-related group, a glucoseaminoglycan group and a proteoglycan group;

(11) In the organic/inorganic hybrid-porous biodegradable polymer scaffold, the size of the basic nano ceramic particle is 1 nm to 1 mm;

(12) In the organic/inorganic hybrid-porous biodegradable polymer scaffold, the basic ceramic nanoparticles are 1 to 99 parts by weight, the animal tissue or cell-derived bioactive extracellular matrix material is 1 to 99 parts by weight, and the biodegradable polymer is 1 to 99 parts by weight with respect to 100 parts by total weight of the organic/inorganic hybrid-porous biodegradable polymer scaffold;

(13) A biomedical implant includes the above-described organic/inorganic hybrid-porous biodegradable polymer scaffold;

(14) The biomedical implant is one or more selected from a scaffold for tissue regeneration, a stent, a suture for surgical operation, a bio nanofiber, a hydrogel, a bio sponge, a pin, a screw, a bar, an implant, and a medical supply;

(15) A method for preparing an organic/inorganic hybrid-porous biodegradable polymer scaffold, which includes:
  (a) preparing an organic/inorganic hybrid polymer solution by dissolving or suspending basic ceramic nanoparticles, an animal tissue or cell-derived bioactive first extracellular matrix material, a biodegradable polymer and a pore inducer in an organic solvent;
  (b) preparing a porous biodegradable polymer scaffold by lyophilizing an organic/inorganic hybrid polymer to remove the pore inducer; and
  (c) culturing and decellularizing cells on the porous biodegradable polymer scaffold to coat a pore inner wall with a second extracellular matrix material.

(16) In the method for preparing an organic/inorganic hybrid-porous biodegradable polymer scaffold, the pore inducer is ice particles.

(17) In the method for preparing an organic/inorganic hybrid-porous biodegradable polymer scaffold, the pore inducer includes a second extracellular matrix material and ice particles.

(18) Step (c) is for culturing cells while the porous biodegradable polymer scaffold is immersed in a cell culture medium, wherein the cell culture medium includes one or more selected from the group consisting of angiopoietin, a bone morphogenetic protein (BMP), a granulocyte colony stimulating factor (G-CSF), a granulocyte macrophage colony-stimulating factor (GM-CSF), an epidermal growth factor (EGF), ephrin, erythropoietin, a fibroblast growth factor (FGF), a hepatocyte growth factor (HGF), an insulin-like growth factor (IGF), a keratinocyte growth factor (KGF), a nerve growth factor (NGF), a placental growth factor (PGF), a platelet-derived growth factor (PDGF), a transforming growth factor (TGF), a tumor necrosis factor-alpha (TNF-$\alpha$) and a vascular endothelial growth factor (VEGF).

(19) A method for preparing an organic/inorganic hybrid-porous biodegradable polymer scaffold, which includes:
  (a) preparing an organic/inorganic hybrid polymer solution by dissolving or suspending a pore inducer including basic ceramic nanoparticles, an animal tissue or cell-derived bioactive first extracellular matrix material, a biodegradable polymer and a second extracellular matrix material in an organic solvent; and
  (b) lyophilizing the organic/inorganic hybrid polymer solution to remove the pore inducer and coat a pore inner wall with the second extracellular matrix material.

DETAILED DESCRIPTION OF EXEMPLARY EMBODIMENTS

Hereinafter, the present invention will be described in detail. First, terminology or terms used in the specification and claims should not be interpreted by conventional or dictionary meanings but should be interpreted by the meanings and concepts corresponding to the technical idea of the present invention based on the principle in that an inventor can properly define the definitions of the terms to explain his/her own invention by the best method. Therefore, embodiments described in the specification and configurations illustrated in the embodiments and drawings in the specification are merely the most exemplary embodiments of the present invention, not representing all of the technical ideas of the present invention. It should be understood that at the time of application, there may be various modifications and variations that are able to substitute the embodiments.

The present invention relates to an organic/inorganic hybrid-porous biodegradable polymer scaffold, which includes basic ceramic nanoparticles, an animal tissue or cell-derived bioactive first extracellular matrix material and a biodegradable polymer, and in which inner walls of pores are coated with a second extracellular matrix material. The basic ceramic nanoparticles used in the present invention are one or more types of metal particles selected from the group consisting of alkali metals and alkali earth metals or one or more types of basic metal compound particles selected from hydroxides of alkali metals, oxides of alkali metals, hydroxides of alkali earth metals and oxides of alkali earth metals.

The alkali metal or alkali earth metal may be lithium (Li), beryllium (Be), sodium (Na), magnesium (Mg), potassium (K), calcium (Ca), rubidium (Rb), strontium (Sr), barium (Ba), cesium (Cs), francium (Fr) or radium (Ra). Also, the oxide of an alkali metal or an alkali earth metal, the hydroxide of an alkali metal or an alkali earth metal or the compound containing an alkali metal may be one or more selected from the group consisting of lithium hydroxide, beryllium hydroxide, sodium hydroxide, magnesium hydroxide, potassium hydroxide, calcium hydroxide, rubidium hydroxide, strontium hydroxide, barium hydroxide, cesium hydroxide, francium hydroxide, radium hydroxide, magnesium oxide, sodium oxide, lithium oxide, manganese oxide, potassium oxide, calcium oxide, barium oxide, cesium oxide, radium oxide, magnesium sulfoxide, magnesium chloride, magnesium carbonate, magnesium bromide, magnesium stearate, magnesium perchlorate, magnesium citrate, magnesium phosphate, magnesium nitrate, magnesium nitride, magnesium iodide, magnesium acetate, magnesium ethoxide, magnesium fluoride, magnesium hydride, manganese monoperoxyphthalate, boron magnesium hydroxide, magnesium silicide, magnesium boride, magnesium aluminate, magnesium methylate, magnesium methalocyanine, magnesium salicylate, magnesium hexafluorosilicate, struvite, huntite, whitlockite, bredigite, dolomite, calcium carbonate, fluorspar, tricalcium phosphate and hydroxyapatite.

Here, when the basic ceramic nanoparticles have a diameter of 1 mm or more, precipitation occurs due to the weight of the basic ceramic nanoparticles, resulting in phase separation from an organic solvent. Therefore, the size of the basic nano ceramic particle used in the present invention may be 1 mm or less. Here, the size of the basic ceramic nanoparticles refers to those of particles modified by a fatty acid and particles modified by a polymer as well as particles before modification.

To enhance dispersity and stability of the basic ceramic nanoparticles in an organic solvent, surfaces of the basic ceramic nanoparticles may be modified by a fatty acid, which may be one or more selected from the group consisting of caprylic acid, capric acid, lauric acid, myristoleic acid, palmitoleic acid, sapienic acid, oleic acid, elaidic acid, vaccenic acid, linoleic acid, ricinoleic acid, linoelaidic acid, α-linoleic acid, arachidonic acid, eicosapentaenoic acid, erucic acid, palmitate, stearic acid, DHA, octadecanoic acid, coconut oil, palm oil, cotton seed oil, wheat germ oil, bean oil, olive oil, corn oil, sunflower oil, safflower oil, hampseed oil and canola oil.

The basic ceramic nanoparticles whose surface is modified by a fatty acid can be prepared by reacting 1 to 95 parts by weight of the fatty acid with the ceramic nanoparticles through esterification.

The basic ceramic nanoparticles according to the present invention are basic ceramic nanoparticles maintaining high dispersity and high stability in an organic solvent, which may be one or more selected from the following examples: alcohols such as methanol, ethanol, propanol and butanol; aldehydes such as ammonia, dimethylsulfoxide, dimethylformamide, acetonitrile, tetrahydrofuran, formaldehyde, glutaldehyde and acetaldehyde; alkanes such as dioxane, chloroform, heptane, hexane, pentane, octane, nonane and decane; benzene ring-based solvents such as benzene, toluene and xylene; ethers such as ether, di-propyl ether, petroleum ether and methyl-t-butyl ether; ketones such as propanone, butanone, pentanone, hexanone and heptanone; and conventional organic solvents such as methylene chloride, perfluoroisopropane and carbon tetrachloride.

Also, the basic ceramic nanoparticles or fatty acid-modified basic ceramic nanoparticles surface-modified with a polymer material, which may be a polymer material formed by polymerization of one or more monomers selected from the group consisting of L-lactide, D-lactide, D,L-lactide, glycolide, caprolactone, dioxanone, trimethylene carbonate, hydroxyalkanoate, peptide, cyanoacrylate, lactic acid, glycolic acid, hydroxycaproic acid, maleic acid, phosphazene, amino acid, hydroxybutyric acid, sebacic acid, hydroxyethoxyacetic acid and trimethylene glycol. Specifically, the polymer used for surface modification of the basic ceramic nanoparticles may be one or more selected from the group consisting of poly-L-lactide, poly-D-lactide, poly-D,L-lactide, polyglycolide, polycaprolactone, poly-L-lactide-co-glycolide, poly-D-lactide-co-glycolide, poly-D,L-lactide-co-glycolide, poly-L-lactide-co-caprolactone, poly-D-lactide-co-caprolactone, poly-D,L-lactide-co-caprolactone, poly(glycolide-co-caprolactone), polydioxanone, polytrimethylene carbonate, poly(glycolide-co-dioxanone), polyamideester, polypeptide, polyorthoester, polymaleic acid, polyphosphazene, polyanhydride, polycebacicanhydride, polyhydroxyalkanoate, polyhydroxybutylate and polycyanoacrylate.

An animal tissue or cell-derived bioactive first extracellular matrix material used in the present invention is a matrix protein made from animal tissue or cells available in a combined state or an artificially-isolated single molecular state, and a protein may have a natural structure or a modified structure.

The matrix protein may be one or more selected from the group consisting of a group having a fiber structure, glucoseaminoglycan group and proteoglycan group.

As the group having a fiber structure, one or more selected from collagen fiber, elastin fiber, laminin, fibrogen, fibronectin and gelatin may be used. Here, the collagen may be I, II, III, IV, V, VI, VII, VIII, IX, X, XI, XII, XIV, XV, XVI, XVIII, XIX, XX, XXI, XXII, XXIII, XXIV, XXV, XXVI, XXVII, XXVIII collagen by types.

As the osteogenic differentiation and ossification-related group, one or more selected from osteonectin, osteofontin, vitronectin and vimentin may be used. As the glucoseaminoglycan group, one or more selected from heparan sulfoxide, keratan sulfoxide, chondroitin sulfoxide, dermatan sulfoxide, heparin, low-molecular heparin and hyaluronic acid may be used.

As the proteoglycan group, one or more selected from dekolin, biglycan, versican, tertican, perlecan, bikunin, neurocan, aggrecan, fibromodulin and lumican may be used. Also, the matrix protein-mixed form may be Matrigel, and other extracellular matrix materials may be used after decellularization performed after tissue or cell culture.

In the present invention, animal-derived tissue may be derived from a spinal animal such as a pig, a cow, a rat, sheep, a horse, a dog or a cat, and may be, depending on a purpose, amniotic sac, skin, small intestinal submucosa tissue, fasia or meninges.

In the present invention, the cells constituting the decellularized second extracellular matrix, which is coated on the pore surface may be one or more selected from the group consisting of fibroblast, vascular endothelial cells, epithelia cells, cartilage cells, osteoblasts, smooth muscle cells, cardiomyocyte, liver cells, nerve cells, intervertebral disc cells, vascular endothelial cells, vascular endothelial progenitor cells, renal progenitor cells, pancreatic progenitor cells, neural progenitor cells, cardiac progenitor cells, adipose-derived stem cells, bone marrow-derived stem cells, mesenchymal stem cells, induced pluripotent stem cells and embryonic stem cells.

Also, an ice particle pore inducer used in the present invention is a group prepared from a solution in which a natural polymer constituting the second extracellular matrix is dissolved may be one or more selected from the group consisting of extracellular matrix-based proteins including collagen, gelatin, elastin, silk, keratin, fibrinogen, hyaluronic acid, alginate, dextran, chondroitin sulfate, heparan sulfate, keratan sulfate, dextran sulfate, a protein based on an extracellular matrix including fibronectin, laminin, polysaccharides and a glycoprotein group.

In the present invention, a bioactive material contained in the porous organic/inorganic hybrid scaffold in the preparation of the pore inducer and included in a cell culture medium may be one or more selected from angiopoietin, bone morphogenetic protein (BMP), a granulocyte colony stimulating factor (G-CSF), a granulocyte macrophage colony-stimulating factor (GM-CSF), epidermal growth factor (EGF), ephrin, erythropoietin, a fibroblast growth factor (FGF), a hepatocyte growth factor (HGF), an insulin-like growth factor (IGF), a keratinocyte growth factor (KGF), nerve growth factor (NGF), a placental growth factor (PGF), a platelet-derived growth factor (PDGF), a transforming growth factor (TGF), a tumor necrosis factor-alpha (TNF-α) and a vascular endothelial growth factor (VEGF).

In the present invention, decellularization of the second extracellular matrix material may be performed by a physical decellularizing method, a chemical decellularizing method or a combination of the physical and chemical methods.

The physical decellularizing method may include a freeze-thaw method, ultrasonication, or physical stirring. The chemical decellularizing method may include treatment with a hypotonic solution prepared by dissolving animal-derived tissue powder in water, an anionic surfactant, a non-ionic surfactant, a cationic surfactant, DNase, RNase or trypsin. Also, the decellularization step may be performed at a temperature range from approximately 0 to 50° C. In the chemical decellularizing method, as the hypotonic solution, a tris HCl (pH 8.0) solution may be used, and as the anionic surfactant, sodium dodecylsulfate (SDS), sodium deoxycholate, or Triton X-200 may be used. Also, as the non-ionic surfactant, Triton X-100, Tween 20 or Tween 80 may be used, and as the cationic surfactant, CHAPS, sulfobetaine-10 (SB-10), SB-16, tri-n-butyl phosphate, N-lauroyl-sarcosinate, or Igepal CA630 may be used.

Also, following taking animal tissue, for example, renal tissue, the decellularization may be performed before, after, or at the same time as micronizing.

The present invention provides a porous organic/inorganic hybrid biomedical implant composed of the modified ceramic particles having high dispersity and high stability and a biodegradable polymer material, and the biomedical implant may be used as a material for the biomedical implant itself or may be coated on a surface of the biomedical implant.

The biodegradable polymer used in the porous scaffold of the present invention may be one or more selected from the group consisting of poly-L-lactide, poly-D-lactide, poly-D,L-lactide, polyglycolide, polycaprolactone, poly-L-lactide-co-glycolide, poly-D-lactide-co-glycolide, poly-D,L-lactide-co-glycolide, poly-L-lactide-co-caprolactone, poly-D-lactide-co-caprolactone, poly-D,L-lactide-co-caprolactone, poly(glycolide-co-caprolactone), polydioxanone, polytrimethylene carbonate, poly(glycolide-co-dioxanone), polyamideester, polypeptide, polyorthoester, polymaleic acid, polyphosphazene, polyanhydride, polycebacicanhydride, polyhydroxyalkanoate, polyhydroxybutylate and polycyanoacrylate.

The organic/inorganic hybrid biomedical implant including basic ceramic nanoparticles, an extracellular matrix material and a biodegradable polymer according to the present invention may include 1 to 99 parts by weight of ceramic nanoparticles, 1 to 99 parts by weight of an extracellular matrix material, and 1 to 99 parts by weight of a biodegradable polymer.

In the present invention, the modified ceramic nanoparticles having high dispersity and high stability may have a particle size of 1 nm to 1 mm, and a neutralization rate due to basic ceramic particles of an acidic material generated in degradation of the biodegradable polymer may be adjusted to 1 minute to 2 years or longer using solubility differences between ceramic particles in a solvent according to a particle size.

Also, the neutralization degree and rate of the biomedical implant are adjustable by the content of the modified ceramic particles included in the biomedical implant, and generally, as the content of the basic ceramic particles increases, the neutralization degree and rate increase.

Also, the hydrophilicity, mechanical strength and degradation duration of the biomedical implant according to the present invention may be adjusted according to the content of the bioactive extracellular matrix material, and generally, as the content of the extracellular matrix material increases, hydrophilicity becomes higher, mechanical strength becomes lower, and degradation duration also becomes shorter.

The porous scaffold using the organic/inorganic hybrid polymer material of the present invention is prepared as a three-dimensional porous scaffold by lyophilizing a biodegradable polymer solution including ceramic nanoparticles and decellularized animal-derived tissue using ice particles including an extracellular matrix-based material as a pore inducer modifying a pore surface, and cells of specific tissue are implanted and cultured in the resulting scaffold, followed by decellularization, resulting in a porous biodegradable organic/inorganic hybrid scaffold for tissue regeneration, which is surface coated with the extracellular matrix material.

According to the method of the present invention, by using a lyophilization technique using ice particles as a pore inducer, the porous biodegradable polymer scaffold may be more simply prepared, pore size may be easily adjusted, and an open structure between pores, which has a large surface area and high porosity, may be formed. Also, problems of pore blockage, secretion, and retaining of toxic materials occurring on the surface of the prepared scaffold may be solved, and particularly, releasing of the ceramic nanoparticles and the extracellular matrix material, which occurs in the preparation of the biomedical implant, may be prevented, thereby greatly increasing the effectiveness of the biomedical implant. The porous scaffold according to the present invention is formed to have a pore size of 10 to 500 µm, a very large surface area per unit volume, and a high porosity of 90 to 98%.

Hereinafter, the present invention will be described in detail with reference to examples. However, examples according to the present invention may be modified in various forms, and it should not be interpreted that the scope of the present invention is limited to the examples that will be described below. The examples of the present invention are provided for more fully explaining the present invention to those of ordinary knowledge in the art.

Preparation of Magnesium Hydroxide Nanoparticles

Magnesium hydroxide nanoparticles were prepared as follows. A sodium hydroxide solution was prepared by dissolving 10.8 g of sodium hydroxide in 300 ml of deionized water, and a magnesium nitrate solution prepared by dissolving 20 g of magnesium nitrate in 150 ml of deionized water was added dropwise to the sodium hydroxide solution using a dropping funnel at a rate of 40 drops per minute. The magnesium hydroxide nanoparticles precipitated in the reaction solution were obtained by purification with a filter while flowing distilled water. The obtained magnesium hydroxide nanoparticles were dried under vacuum, and then stored.

Preparation of Fatty Acid-Modified Magnesium Hydroxide Particles

Magnesium hydroxide particles modified by ricinoleic acid were prepared by mixing 10 parts by weight of the magnesium hydroxide prepared by the above-described method and 90 parts by weight of ricinoleic acid based on the total weight of a mixture, and stirring the mixture in a round flask under a nitrogen atmosphere at 70° C. for 12 hours. The fatty acid-modified magnesium hydroxide particles were obtained by purification with a filter to remove unreacted ricinoleic acid while flowing ethanol. The obtained fatty acid-modified magnesium hydroxide particles were dried under vacuum, and then stored.

Preparation of Polymer-Modified Magnesium Hydroxide Particles

Magnesium hydroxide nanoparticles surface-modified using L-lactide were prepared as follows. 80 parts by weight of the magnesium hydroxide prepared by the above-described method was mixed with 20 parts by weight of L-lactide based on the total weight of the entire mixture, and a dilution prepared by diluting 0.05 wt % of stannous octoate in toluene with respect to the total weight of the reactants (magnesium hydroxide and L-lactide) as a catalyst was added. A glass ampoule flask containing the reactants was maintained at 70° C. in a vacuum state for 6 hours while stirring to completely remove toluene and moisture. The closed glass ampoule flask was heated in oil maintained at 150° C. and stirred, thereby performing ring-opening polymerization for 48 hours. Retrieved polymer was added to a sufficient amount of chloroform to remove a homopolymer and unreacted residues for over 1 hour.

Preparation of Fatty Acid and Polymer-Modified Magnesium Hydroxide Particles

Fatty acid and polymer-modified magnesium hydroxide nanoparticles were prepared using L-lactide as follows. 80 parts by weight of the fatty acid magnesium hydroxide prepared by the above-described method was mixed with 20 parts by weight of L-lactide based on the total weight of the entire mixture, a dilution prepared by diluting 0.05 wt % of stannous octoate in toluene with respect to the total weight of reactants (magnesium hydroxide and L-lactide) was added as a catalyst. A glass ampoule flask containing the reactants was stirred and maintained at 70° C. under vacuum for 6 hours until toluene and moisture were completely removed. The closed glass ampoule flask was heated in oil at 150° C. while stirring to perform ring-opening polymerization for 48 hours. A retrieved polymer was added to a sufficient amount of chloroform to remove a homopolymer and unreacted residues for over 1 hour.

Preparation of Decellularized and Micronized First Extracellular Matrix

Renal tissue was taken from a kidney of an animal and washed with normal saline three times for 10 minutes. After washing, the renal tissue was dehydrated with ethanol, and to remove renal cells and a gene component present in the tissue and obtain a pure extracellular matrix, decellularization was performed as follows. The dehydrated renal tissue was added to 1 L of 0.1% sodium dodecyl sulfate (SDS) solution per 10 g and stirred at 100 rpm for 24 hours. Following the SDS treatment, the resulting mixture was washed with deionized water 5 times at 100 rpm for 30 minutes, 200 ml of DNase was added at a concentration of 200 U/ml thereto, and then the resulting mixture was stirred at 37° C. and 100 rpm for 24 hours. The resulting precipitate was washed with deionized water 5 times at 100 rpm for 30 minutes. Finally, the dried and decellularized extracellular matrix was micronized to a size of approximately 50 μm using a freezer/mill.

Preparation of Ice Particle Pore Inducer Including Second Extracellular Matrix-Based Material An ice particle pore inducer was prepared using gelatin to prepare a porous scaffold. 0.5, 2 or 5 wt % of a gelatin solution was prepared by adding 5, 20 or 50 g of gelatin to 1 L of distilled water, and the mixture was stirred at 50° C. and 300 rpm. Gelatin ice particles were prepared by transferring a gelatin solution to a microspray, and directly spraying the gelatin solution to liquid nitrogen. The prepared gelatin ice particles were sequentially transferred from a cold chamber to micro standard sieves with different sizes to divide the gelatin ice particles by sizes. 0.5, 2, or 5 wt % of the gelatin ice particles were divided into less than 100 μm size, 100-200 μm size, 200-300 μm size, 300-400 μm size, or 400-500 μm size, and stored at −80° C. to prepare a scaffold, together with an organic/inorganic polymer solution.

Preparation of Organic/Inorganic Hybrid Polymer Porous Scaffold

A porous scaffold using an organic/inorganic hybrid polymer material was prepared by a lyophilization technique using distilled water or gelatin ice particles as a pore inducer. Distilled water or gelatin ice particles of 200-300 μm size were uniformly mixed with a biodegradable polymer solution including the magnesium hydroxide particles prepared as described above and the micronized extracellular matrix material, put into a silicone mold to determine the size and shape thereof in liquid nitrogen, and lyophilized at 0° C. under 5 mTorr, thereby preparing the porous scaffold.

Preparation of Decellularized Second Extracellular Matrix-Coated Porous Scaffold A scaffold in which surfaces of pores was coated with an extracellular matrix was prepared by implanting and culturing cells in a porous scaffold having pores formed with distilled water or gelatin ice particles and performing decellularization. Following being sterilized with ethylene oxide gas, the porous scaffold was immersed in phosphate-buffered saline (PBS) and a cell culture medium to be in a wet state, and then $5\times10^5$ of fibroblasts were implanted. The cell-seeded scaffold was cultured in a 5% $CO_2$ incubator at 37° C. for 3 days. Afterward, the cell-cultured scaffold was washed with PBS, and immersed in a solution, in which 0.4 mM ammonia was mixed with 0.25% Triton X-100, for 10 minutes for decellularization. The scaffold was washed again with PBS, treated with a nuclease solution, in which DNase/RNase were dissolved at 50 units/ml and 125 μl/ml, respectively, for 24 hours to completely remove nuclei from the cells. The scaffold in which the pore surface was coated with the extracellular matrix material through decellularization was sufficiently washed with PBS, sealed in a sterilized state, and then stored at −20° C.

Evaluation Methods

The sizes of the prepared ceramic nanoparticles were identified using a nanoparticle analyzer or particle size analyzer (Malvern Zen 3600 Zetasizer, Zetasizer Ivano, UK).

To confirm stability of the ceramic particles in an organic solvent, ceramic particles were mixed with a conventional organic solvent, particularly; an organic solvent such as methanol, ethanol, propanol, dimethylsulfoxide, dimethylformamide, acetonitrile, tetrahydrofuran, dioxane, chloroform, hexane, toluene, xylene, ether or methylene chloride, and the precipitation of the particles was evaluated at room temperature for 4 weeks.

Also, to confirm remaining cells and gene components of the extracellular matrix material, fluorescent imaging was used, and to confirm cytotoxicity, in vitro evaluation using fibroblasts was performed.

To evaluate properties of the prepared biomedical implant, mechanical tensile strength was measured using Intron according to the method regulated by ASTM D638, and change in water contact angle, biodegradation duration and pH change were examined. Also, cellular inflammatory response and cytotoxicity were evaluated by the degree of expression of inflammatory factors and a cytotoxicity test, respectively.

The pore size and structure of the porous biodegradable polymer scaffold were analyzed using a scanning electron microscope, and the porosity was measured using a mercury porosimeter. Also, the loss of ceramic nanoparticles in the preparation of the scaffold was examined through an elementary analysis. As a result, it was confirmed that the pore sizes were uniformly 100 to 300 μm, and there was the proper interconnection between pores. Also, the porosity was evaluated as high as 90 to 98%. Also, it was confirmed that the magnesium content remaining in the scaffold was similar to the initial supply, which means that there was almost no loss.

The structure of a pore surface of the scaffold which was coated with a decellularized extracellular matrix by coating with a pore inducer including an extracellular matrix-based natural polymer material or with the implantation and culture of cells was analyzed using a scanning electron microscope. The material derived from the extracellular matrix coated on the pore surface was visualized by fluorescent imaging, and a matrix protein induced to the scaffold was quantified by a micro BCA analysis.

To evaluate the tissue regeneration capability, the prepared porous biodegradable polymer scaffold was implanted to a renal damage model. The scaffold was sterilized with ethylene oxide gas and ethanol and immersed in normal saline for prewaiting. Nephrectomy was performed on a rat, which was a laboratory animal, and a scaffold having a size of 5×2×2 mm$^3$ was implanted to a partially damaged part of the renal cortex. After 1, 2, 4, 8 or 12 weeks, a histological analysis was performed to evaluate extracted tissue through immunohistochemistry and polymerase chain reaction (PCR).

Biomedical implants prepared in the following examples were prepared for renal regeneration, but it is obvious that the present invention is not limited to the scope of these examples, and biomedical implants for target tissue needing implanting could be prepared by using a proper animal tissue or cell-derived bioactive extracellular matrix material of an organ for regeneration, as needed.

Example 1

A porous biodegradable polymer scaffold was prepared by mixing 15 parts by weight of the magnesium hydroxide ceramic nanoparticles prepared by the above-described method and 0.2 to 10 parts by weight of decellularized extracellular matrix powder prepared from a pig kidney with 90 to 99.8 parts by weight of a polylactide-co-glycolide (50:50) biodegradable polymer having a molecular weight of 40 kDa and coating surfaces of pores with an extracellular matrix-based material, collagen by the above-described method using 0.5% collagen ice particle pore inducer including angiopoietin.

The degradation duration of the prepared porous biodegradable polymer scaffold was 2 months, the prepared scaffold exhibited pH neutralizing effect, completely inhibited inflammatory response, and no cytotoxicity. Also, it was confirmed that the polymer scaffold showed improved cell adhesion capability/tissue regeneration capability, and improved hydrophilicity and compressive strength.

Example 2

A porous biodegradable polymer scaffold was prepared by mixing 15 parts by weight of the magnesium oxide ceramic nanoparticles prepared by the above-described method and 0.2 to 10 parts by weight of decellularized extracellular matrix powder prepared from a pig lung with 90 to 99.8 parts by weight of a polylactide-co-glycolide (75:25) biodegradable polymer having a molecular weight of 40 kDa and coating surfaces of pores with an extracellular matrix-based material, hyaluronic acid, using a 2% hyaluronic acid ice particle pore inducer including a bone morphogenetic protein. The prepared porous biodegradable polymer scaffold was degraded over 2 months. The prepared scaffold exhibited pH neutralizing effect, completely inhibited inflammatory response, and had no cytotoxicity. Also, the polymer scaffold showed excellent cell adhesion and tissue regeneration capabilities, and considerably improved hydrophilicity and compressive strength.

Example 3

A porous biodegradable polymer scaffold was prepared by mixing 15 parts by weight of the magnesium hydroxide ceramic nanoparticles whose surface was modified by linoleic acid prepared by the above-described method and 0.2 to 10 parts by weight of decellularized extracellular matrix powder prepared from a rat kidney with 90 to 99.8 parts by weight of a polylactide-co-glycolide (50:50) biodegradable polymer having a molecular weight of 80 kDa and coating surfaces of pores with an extracellular matrix-based material, fibronectin, using a 0.5% fibronectin ice particle pore inducer including a liver cell growth factor. The prepared porous biodegradable polymer scaffold was degraded over 2 months. The prepared scaffold exhibited pH neutralizing effect, completely inhibited inflammatory response, and had no cytotoxicity. Also, the polymer scaffold showed excellent cell adhesion and tissue regeneration capabilities, and considerably improved hydrophilicity and compressive strength.

Example 4

A porous biodegradable polymer scaffold was prepared by mixing 15 parts by weight of the magnesium hydroxide ceramic nanoparticles whose surface was modified by oleic acid prepared by the above-described method and 0.2 to 10 parts by weight of decellularized extracellular matrix powder prepared from a rabbit liver with 90 to 99.8 parts by weight of a polylactide-co-glycolide (85:15) biodegradable polymer having a molecular weight of 100 kDa and coating surfaces of pores with an extracellular matrix-based material, laminin, using a 0.5% laminin ice particle pore inducer including a fibroblast growth factor. The prepared porous biodegradable polymer scaffold was degraded over 2 months. The prepared scaffold exhibited pH neutralizing effect, completely inhibited inflammatory response, and had no cytotoxicity. Also, the polymer scaffold showed excellent cell adhesion and tissue regeneration capabilities and considerably improved hydrophilicity and compressive strength.

Example 5

A porous biodegradable polymer scaffold was prepared by mixing 15 parts by weight of the magnesium hydroxide ceramic nanoparticles whose surface was modified by stearic acid prepared by the above-described method and 0.2 to 10 parts by weight of decellularized extracellular matrix powder prepared from a pig kidney with 90 to 99.8 parts by weight of a polylactide-co-caprolactone (50:50) biodegradable polymer having a molecular weight of 60 kDa,—and coating surfaces of pores with an extracellular matrix-based material, gelatin, using a 5% gelatin ice particle pore inducer. The prepared porous biodegradable polymer scaffold was degraded over 2 months. The prepared scaffold exhibited pH neutralizing effect, completely inhibited inflammatory response, and had no cytotoxicity. Also, the polymer scaffold showed excellent cell adhesion and tissue regeneration capabilities and considerably improved hydrophilicity and compressive strength.

Example 6

A porous biodegradable polymer scaffold was prepared by mixing 15 parts by weight of the magnesium hydroxide ceramic nanoparticles whose surface was modified by ricinoleic acid prepared by the above-described method and 0.2 to 10 parts by weight of decellularized extracellular matrix powder prepared from a pig liver with 90 to 99.8 parts by weight of a polylactide-co-caprolactone (75:25) biodegradable polymer having a molecular weight of 30 kDa. $5 \times 10^5$ of fibroblasts were implanted and cultured in the prepared scaffold using a culture medium including an insulin-like growth factor, and after three days, decellularization was performed by the above-described method, thereby obtaining a porous scaffold in which surfaces of pores were coated with an extracellular matrix. The prepared porous biodegradable polymer scaffold was degraded over 2 months. The prepared scaffold exhibited pH neutralizing effect, completely inhibited inflammatory response, and had no cytotoxicity. Also, the polymer scaffold showed excellent cell adhesion and tissue regeneration capabilities and considerably improved hydrophilicity and compressive strength.

Example 7

A porous biodegradable polymer scaffold was prepared by mixing 15 parts by weight of the magnesium oxide ceramic nanoparticles whose surface was modified by stearic acid prepared by the above-described method and 0.2 to 10 parts by weight of decellularized extracellular matrix powder prepared from a rabbit heart with 90 to 99.8 parts by weight of a polylactide-co-glycolide (65:35) biodegradable polymer having a molecular weight of 100 kDa. $2 \times 10^6$ of cartilage cells were implanted and cultured in the prepared scaffold using a culture medium including a nerve growth factor, and after 3 days, decellularization was performed as described above, thereby obtaining a porous scaffold in which surfaces of pores were coated with an extracellular matrix. The porous biodegradable polymer scaffold was degraded over 2 months. The prepared scaffold exhibited pH neutralizing effect, completely inhibited inflammatory response, and had no cytotoxicity. Also, the polymer scaffold showed excellent cell adhesion and tissue regeneration capabilities and considerably improved hydrophilicity and compressive strength.

Example 8

A porous biodegradable polymer scaffold was prepared by mixing 15 parts by weight of the magnesium hydroxide ceramic nanoparticles whose surface was modified by polylactide prepared by the above-described method and 0.2 to 10 parts by weight of decellularized extracellular matrix powder prepared from a pig lung with 90 to 99.8 parts by weight of a poly(L-lactic acid) biodegradable polymer having a molecular weight of 200 kDa. $1 \times 10^6$ of vascular endothelial cells were implanted and cultured in the prepared scaffold using a culture medium including a platelet-derived growth factor, and after 3 days, decellularization was performed as described above, thereby obtaining a porous scaffold in which surfaces of pores were coated with an extracellular matrix. The porous biodegradable polymer scaffold was degraded over 2 months. The prepared scaffold exhibited pH neutralizing effect, completely inhibited inflammatory response, and no cytotoxicity. Also, the polymer scaffold showed excellent cell adhesion and tissue regeneration capabilities and considerably improved hydrophilicity and compressive strength.

Example 9

A porous biodegradable polymer scaffold was prepared by mixing 15 parts by weight of the magnesium oxide ceramic nanoparticles whose surface was modified by polylactide prepared by the above-described method and 0.2 to 10 parts by weight of decellularized extracellular matrix powder prepared from a rat kidney with 90 to 99.8 parts by weight of a polycaprolactone biodegradable polymer having a molecular weight of 180 kDa. $1 \times 10^6$ of osteoblasts were implanted and cultured in the prepared scaffold using a culture medium including a transforming growth factor, and after 3 days, decellularization was performed as described above, thereby obtaining a porous scaffold in which surfaces of pores were coated with an extracellular matrix. The porous biodegradable polymer scaffold was degraded over 2 months. The prepared scaffold exhibited pH neutralizing effect, completely inhibited inflammatory response, and had no cytotoxicity. Also, the polymer scaffold showed excellent cell adhesion and tissue regeneration capabilities and considerably improved hydrophilicity and compressive strength.

Example 10

A porous biodegradable polymer scaffold was prepared by mixing 15 parts by weight of the magnesium hydroxide ceramic nanoparticles whose surface was modified by ricinoleic acid and polylactide prepared by the above-described method and 0.2 to 10 parts by weight of decellularized extracellular matrix powder prepared from a pig heart with 90 to 99.8 parts by weight of a poly(DL-lactic acid) biodegradable polymer having a molecular weight of 350 kDa. $5 \times 10^5$ of adipose-derived stem cells were implanted and cultured in the prepared scaffold, and after 3 days, decellularization was performed as described above, thereby obtaining a porous scaffold in which surfaces of pores were coated with an extracellular matrix. The porous biodegradable polymer scaffold was degraded over 2 months. The prepared scaffold exhibited pH neutralizing effect, completely inhibited inflammatory response, and had no cytotoxicity. Also, the polymer scaffold showed excellent cell adhesion and tissue regeneration capabilities and considerably improved hydrophilicity and compressive strength.

Example 11

A porous biodegradable polymer scaffold was prepared by mixing 15 parts by weight of the magnesium hydroxide ceramic nanoparticles whose surface was modified by stearic acid and polylactide prepared by the above-described method and 0.2 to 10 parts by weight of decellularized extracellular matrix powder prepared from a rabbit kidney with 90 to 99.8 parts by weight of a polylactide-caprolactone (75:25) biodegradable polymer having a molecular weight of 30 kDa and coating surfaces of pores with gelatin using a 5% chondroitin gelatin ice particle pore inducer. $5\times10^5$ of fibroblasts were implanted and cultured in the prepared scaffold using a culture medium including a fibroblast growth factor, and after 3 days, decellularization was performed as described above, thereby obtaining a porous scaffold in which surfaces of pores were coated with an extracellular matrix. The porous biodegradable polymer scaffold was degraded over 2 months. The prepared scaffold exhibited pH neutralizing effect, completely inhibited inflammatory response, and had no cytotoxicity. Also, the polymer scaffold showed excellent cell adhesion and tissue regeneration capabilities and considerably improved hydrophilicity and compressive strength.

Example 12

A porous biodegradable polymer scaffold was prepared by mixing 15 parts by weight of the magnesium hydroxide ceramic nanoparticles whose surface was modified by polylactide prepared by the above-described method and 0.2 to 10 parts by weight of decellularized extracellular matrix powder prepared from a pig lung with 90 to 99.8 parts by weight of a polylactide-co-glycolide (50:50) biodegradable polymer having a molecular weight of 100 kDa and coating surfaces of pores with chondroitin sulfate using a 2% chondroitin sulfate ice particle pore inducer. $1\times10^6$ of vascular endothelial progenitor cells were implanted and cultured in the prepared scaffold using a culture medium including a vascular endothelial growth factor, and after 3 days, decellularization was performed as described above, thereby obtaining a porous scaffold in which surfaces of pores were coated with an extracellular matrix. The porous biodegradable polymer scaffold was degraded over 2 months. The prepared scaffold exhibited pH neutralizing effect, completely inhibited inflammatory response, and had no cytotoxicity. Also, the polymer scaffold showed excellent cell adhesion and tissue regeneration capabilities and considerably improved hydrophilicity and compressive strength.

Example 13

A porous biodegradable polymer scaffold was prepared by mixing 15 parts by weight of the magnesium hydroxide ceramic nanoparticles whose surface was modified by ricinoleic acid prepared by the above-described method and 0.2 to 10 parts by weight of decellularized extracellular matrix powder prepared from a rat kidney with 90 to 99.8 parts by weight of a polylactide-co-glycolide (40 kDa, 50:50) biodegradable polymer having a molecular weight of 100 kDa and coating a pore surface with heparan sulfate using a 5% heparan sulfate ice particle pore inducer. $5\times10^5$ of renal progenitor cells were implanted and cultured in the prepared scaffold using a culture medium including a vascular endothelial growth factor, and after 3 days, decellularization was performed as described above, thereby obtaining a porous scaffold in which surfaces of pores were coated with an extracellular matrix. The porous biodegradable polymer scaffold was degraded over 2 months. The prepared scaffold exhibited pH neutralizing effect, completely inhibited inflammatory response, and had no cytotoxicity. Also, the polymer scaffold showed excellent cell adhesion and tissue regeneration capabilities and considerably improved hydrophilicity and compressive strength.

Example 14

A porous biodegradable polymer scaffold was prepared by mixing 15 parts by weight of the magnesium oxide ceramic nanoparticles whose surface was modified by ricinoleic acid and polylactide prepared by the above-described method and 0.2 to 10 parts by weight of decellularized extracellular matrix powder prepared from a pig liver with 90 to 99.8 parts by weight of a poly(L-lactic acid) biodegradable polymer having a molecular weight of 200 kDa and coating a pore surface with collagen using a 5% collagen ice particle pore inducer. $1\times10^6$ of bone marrow-derived stem cells were implanted and cultured in the prepared scaffold using a culture medium including a transforming growth factor, and after 3 days, decellularization was performed as described above, thereby obtaining a porous scaffold in which surfaces of pores was coated with an extracellular matrix. The porous biodegradable polymer scaffold was degraded over 2 months. The prepared scaffold exhibited pH neutralizing effect, completely inhibited inflammatory response, and had no cytotoxicity. Also, the polymer scaffold showed excellent cell adhesion and tissue regeneration capabilities and considerably improved hydrophilicity and compressive strength.

Example 15

A porous biodegradable polymer scaffold was prepared by mixing 15 parts by weight of the magnesium oxide ceramic nanoparticles whose surface was modified by stearic acid and polylactide prepared by the above-described method and 0.2 to 10 parts by weight of decellularized extracellular matrix powder prepared from a pig kidney with 90 to 99.8 parts by weight of a polylactide-caprolactone (168 kDa, 90:10) biodegradable polymer and coating a pore surface with fibronectin using a 5% fibronectin ice particle pore inducer. $5\times10^5$ of induced pluripotent stem cells were implanted and cultured in the prepared scaffold, and after 3 days, decellularization was performed as described above, thereby obtaining a porous scaffold in which surfaces of pores were coated with an extracellular matrix. The porous biodegradable polymer scaffold was degraded over 2 months. The prepared scaffold exhibited pH neutralizing effect, completely inhibited inflammatory response, and had no cytotoxicity. Also, the polymer scaffold showed excellent cell adhesion and tissue regeneration capabilities and considerably improved hydrophilicity and compressive strength.

Comparative Example 1

A scaffold was prepared using a polylactide-co-glycolide (40 kDa, 50:50) biodegradable polymer alone to measure pH change, inflammatory response, cytotoxicity, and tensile strength.

The prepared scaffold had severely inadequate mechanical properties. Two weeks later, the scaffold exhibited strong acidity of pH 3.7 or less, very high inflammatory response, and cytotoxicity.

Comparative Example 2

A scaffold was prepared by mixing a polylactide-co-glycolide (100 kDa, 50:50) biodegradable polymer with magnesium hydroxide ceramic nanoparticles to measure pH change, inflammatory response, cytotoxicity, and tensile strength. The prepared scaffold was greatly improved in terms of mechanical properties. Two weeks later, the scaffold exhibited a high neutralizing effect of pH 7.0 or more. Inflammatory response was completely inhibited, cytotoxicity was not exhibited, but the tissue regeneration capability was not improved, either.

Comparative Example 3

A scaffold was prepared by mixing a poly(L-lactide) (200 kDa) biodegradable polymer with a pig kidney-derived extracellular matrix material to measured pH change, inflammatory response, cytotoxicity, and tensile strength. The prepared scaffold was improved by a small amount in terms of mechanical properties. Initial pH was neutral at 7.2, and two weeks later, the scaffold exhibited strong acidity of pH 4.0 or less, very high inflammatory response, and cytotoxicity.

Comparative Example 4

A scaffold was prepared by mixing polylactide-caprolactone (30 kDa, 75:25) biodegradable polymer and magnesium oxide ceramic nanoparticles with a pig liver-derived extracellular matrix material to measured pH change, inflammatory response, cytotoxicity, and tensile strength. The prepared scaffold was improved by a small amount in terms of mechanical properties. Two weeks later, pH was neutral at 7.0, and low inflammatory response and cytotoxicity were exhibited. Cell adhesion capability and tissue regeneration capability were improved by small amounts.

Comparative Example 5

A scaffold in which surfaces of pores were coated with gelatin was prepared by mixing a polycaprolactone (180 kDa) biodegradable polymer and a gelatin pore inducer to measure pH change, inflammatory response, cytotoxicity, and tensile strength. The prepared scaffold had no change in terms of mechanical properties.

The initial pH was neutral as 7.2, and two weeks later, the scaffold exhibited strong acidity of pH 4.0 or less, very high inflammatory response, and cytotoxicity.

Comparative Example 6

A scaffold which was coated with an extracellular matrix material through decellularization after the implantation and culture of cells was prepared using a polylactide-co-glycolide (100 kDa, 85:15) biodegradable polymer alone to measured pH change, inflammatory response, cytotoxicity, and tensile strength. The prepared scaffold had no change in terms of mechanical properties. The initial pH was neutral at 7.2, and two weeks later, the scaffold exhibited strong acidity of pH 4.0 or less, very high inflammatory response, and cytotoxicity.

Comparative Example 7

A scaffold was prepared by mixing a polylactide-co-glycolide (40 kDa, 50:50) biodegradable polymer with a pore inducer including a fibroblast growth factor to measure pH change, inflammatory response, cytotoxicity, and tensile strength. The prepared scaffold had no change in terms of mechanical properties. The initial pH was neutral at 7.2, and two weeks later, the scaffold exhibited strong acidity of pH 4.0 or less, very high inflammatory response, and cytotoxicity.

The configurations of the polymer scaffolds in the examples and the comparative examples are summarized in Table 2, and comparative results of characteristic evaluation are listed in Table 1.

TABLE 1

| Example No. | Biodegradable polymer | Bulk hybrid nano ceramic | Bulk hybrid extracellular matrix | Surface coated pore inducer | Surface coated extracellular matrix | Cellular active material |
|---|---|---|---|---|---|---|
| Example 1 | PLGA (50:50, 40 kDa) | Magnesium hydroxide | Pig kidney-derived | 0.5% collagen | — | Angiopoietin |
| Example 2 | PLGA (75:25, 40 kDa) | Magnesium oxide | Pig lung-derived | 2% hyaluronic acid | — | bone morphogenetic protein |
| Example 3 | PLGA (50:50, 80 kDa) | Ricinoleic acid-Magnesium hydroxide | Rat kidney-derived | 0.5% fibronectin | — | liver-derived cell growth factor |
| Example 4 | PLGA (85:15, 100 kDa) | Oleic acid-Magnesium hydroxide | Rabbit liver-derived | 0.5% laminin | — | Fibroblast growth factor |
| Example 5 | PLCL (50:50, 60 kDa) | Stearic acid-Magnesium hydroxide | Pig kidney-derived | 5% gelatin | — | — |
| Example 6 | PLCL (75:25, 30 kDa) | Ricinoleic acid-Magnesium oxide | Pig liver-derived | — | Fibroblast-derived | Insulin-like growth factor |
| Example 7 | PLGA (65:35, 100 kDa) | Stearic acid-Magnesium oxide | Rabbit heart-derived | — | Cartilage cell-derived | Nerve growth factor |
| Example 8 | PLLA (200 kDa) | Polylactide-Magnesium hydroxide | Pig lung-derived | — | Vascular endothelial progenitor cell-derived | Platelet-derived growth factor |

TABLE 1-continued

| Example No. | Biodegradable polymer | Bulk hybrid nano ceramic | Bulk hybrid extracellular matrix | Surface coated pore inducer | Surface coated extracellular matrix | Cellular active material |
|---|---|---|---|---|---|---|
| Example 9 | PCL (180 kDa) | Polylactide-Magnesium oxide | Rat kidney-derived | — | Osteoblast-derived | Transforming growth factor |
| Example 10 | PDLLA (350 kDa) | Polylactide-Ricinoleic acid-Magnesium hydroxide | Pig heart-derived | — | Adipose stem cell-derived | — |
| Example 11 | PLCL (75:25, 30 kDa) | Polylactide-Stearic acid-Magnesium hydroxide | Rabbit kidney-derived | 5% gelatin | Fibroblast-derived | Fibroblast growth factor |
| Example 12 | PLGA (50:50, 100 kDa) | Polylactide-Magnesium hydroxide | Pig lung-derived | 2% chondroitin sulfate | Vascular endothelial progenitor cell-derived | Vascular endothelial growth factor |
| Example 13 | PLGA (50:50, 40 kDa) | Ricinoleic acid-Magnesium hydroxide | Rat kidney-derived | 5% heparan sulfate | Renal progenitor cell-derived | Platelet-derived growth factor |
| Example 14 | PLLA (200 kDa) | Polylactide-Ricinoleic acid-Magnesium oxide | Pig liver-derived | 0.5% collagen | Bone marrow stem cell-derived | Transforming growth factor |
| Example 15 | PLCL (90:10, 168 kDa) | Polylactide-Stearic acid-Magnesium oxide | Pig kidney-derived | 0.5% fibronectin | Induced pluripotent stem cell-derived | — |
| Comparative Example 1 | PLGA (50:50, 40 kDa) | — | — | — | — | — |
| Comparative Example 2 | PLGA (50:50, 100 kDa) | Magnesium hydroxide | — | — | — | — |
| Comparative Example 3 | PLLA (200 kDa) | — | Pig kidney-derived | — | — | — |
| Comparative Example 4 | PLCL (75:25, 30 kDa) | Magnesium oxide | Pig liver-derived | — | — | — |
| Comparative Example 5 | PCL (180 kDa) | — | — | 5% gelatin | — | — |
| Comparative Example 6 | PLGA (85:15, 100 kDa) | — | — | — | Fibroblast-derived | — |
| Comparative Example 7 | PLGA (50:50, 40 kDa) | — | — | — | — | Fibroblast growth factor |

TABLE 2

| Example No. | *pH neutralization evaluation | Inflammatory response | **Cell adhesion capability | **Tissue regeneration capability | Water contact angle | Compressive strength |
|---|---|---|---|---|---|---|
| Example 1 | First level | Completely inhibited | ○ | ○ | 43 | 74 |
| Example 2 | First level | Completely inhibited | ○ | ○ | 46 | 77 |
| Example 3 | First level | Completely inhibited | ○ | ○ | 44 | 73 |
| Example 4 | First level | Completely inhibited | ○ | ○ | 44 | 72 |
| Example 5 | First level | Completely inhibited | ○ | ○ | 43 | 78 |
| Example 6 | First level | Completely inhibited | ○ | ○ | 45 | 72 |
| Example 7 | First level | Completely inhibited | ○ | ○ | 45 | 73 |
| Example 8 | First level | Completely inhibited | ○ | ○ | 42 | 72 |
| Example 9 | First level | Completely inhibited | ○ | ○ | 44 | 72 |

TABLE 2-continued

| Example No. | *pH neutralization evaluation | Inflammatory response | **Cell adhesion capability | **Tissue regeneration capability | Water contact angle | Compressive strength |
|---|---|---|---|---|---|---|
| Example 10 | First level | Completely inhibited | ○ | ○ | 43 | 74 |
| Example 11 | First level | Completely inhibited | ○ | ○ | 41 | 77 |
| Example 12 | First level | Completely inhibited | ○ | ○ | 42 | 76 |
| Example 13 | First level | Completely inhibited | ○ | ○ | 40 | 78 |
| Example 14 | First level | Completely inhibited | ○ | ○ | 43 | 75 |
| Example 15 | First level | Completely inhibited | ○ | ○ | 41 | 76 |
| Comparative Example 1 | Fourth level | Severe | x | x | 85 | 20 |
| Comparative Example 2 | First level | Completely inhibited | Δ | Δ | 80 | 72 |
| Comparative Example 3 | Fourth level | Severe | Δ | Δ | 51 | 30 |
| Comparative Example 4 | First level | Completely inhibited | Δ | Δ | 52 | 75 |
| Comparative Example 5 | Fourth level | Severe | Δ | Δ | 49 | 27 |
| Comparative Example 6 | Fourth level | Severe | Δ | Δ | 49 | 24 |
| Comparative Example 7 | Fourth level | Severe | x | x | 82 | 21 |

(*First level: pH range of 7.2-7.8 after two weeks, Second level: pH range of 6.5-8.5 after two weeks, Third level: pH range of 5.0-8.5 after two weeks, Fourth level: pH range of 4 or less after two weeks, x: 30% or less cells attached, ○: 50-80% cells attached, *x: 30% or cells died, Δ: 10-30% cells died, ○: 90% or more cells died)

The present invention can provide an intelligent porous biodegradable polymer scaffold, which inhibits inflammatory response to an acidic material generated during a process of biomedical implant degradation, facilitates the adjustment of mechanical strength, includes an extracellular matrix-derived bioactive material of target tissue, and is surface-coated with the extracellular matrix-based material to induce tissue regeneration with high efficiency, resulting in more effective tissue regeneration.

Also, in the present invention, the porous polymer scaffold can have various pore sizes and porosities by adjusting the size and content of ice particles using an organic/inorganic hybrid polymer solution mixed with ice particles including an extracellular matrix-based material as a biocompatible pore inducer, and surfaces of pores of the polymer scaffold can simply be coated by adjusting the type and concentration of the extracellular matrix material included in the ice particles, thereby inducing various bioactivities.

Also, to preparation the porous scaffold, lyophilization using ice particles as a pore inducer is used, and thus release of the basic ceramic nanoparticles and bioactive extracellular matrix material occurring in a process of preparing a biomedical implant that can be generated in a conventional salt foaming method can be prevented.

In addition, in the present invention, bioactivity of the scaffold can be reinforced by coating surfaces of pores of the porous organic/inorganic hybrid scaffold with the extracellular matrix after cells that are seeded on the scaffold to culture and decellularized, extracellular matrices having various chemical compositions and physical configurations can be induced by adjusting the type and culture duration of the cells, and the content of the extracellular matrix can be adjusted. The surface-coated extracellular matrix material can enhance an initial cell adhesion capability, thereby improving cell proliferation capability, and proliferation and differentiation of stem cells and progenitor cells of specific tissue can be induced using microenvironmental topography of the extracellular matrix.

Also, the cell proliferation capability and cell differentiation capability of the organic/inorganic hybrid scaffold can be reinforced by treating a bioactive material present in a culture medium or generated from cells in a cell culture and decellularization to allow the scaffold to carry the bioactive material.

In the present invention, dispersion stability on an organic solvent can be enhanced by modifying the basic ceramic nanoparticles with a general fatty acid or a biodegradable polymer material, mechanical properties of a biodegradable polymer material can be enhanced by mixing the modified basic ceramic nanoparticles with the biodegradable polymer material, and inflammatory response and cytotoxicity in the body can be considerably reduced by neutralizing and thus inhibiting an acidic material generated by degrading the biodegradable polymer into basic ceramic nanoparticles.

Also, in the present invention, a bioactive extracellular matrix material obtained from animal tissue or cells is mixed with a biodegradable polymer material to adjust degradation duration, a biomedical implant having enhanced hydrophilicity and tissue regeneration capability is provided to facilitate cell penetration and adhesion, and cell migration after implantation into the body, actively provide oxygen and nutrients, make it easy to culture cells in the scaffold and stimulate cell growth, and thus the resulting mixture can be useful as a scaffold for tissue regeneration.

Therefore, according to the present invention, a porous biodegradable biomedical implant having an inflammatory response inhibitory effect, reinforced physical properties, excellent hydrophilicity, and an improved tissue regeneration capability can be provided. Also, the biomedical implant according to the present invention can be used as materials for cardiovascular surgery such as stents, sutures for surgical operation, scaffolds for tissue regeneration, bio nanofibers, hydrogels or bio sponge, dental materials such as pins, screws, bars, implants and medical supplies, and materials for neurosurgery, orthopedics or plastic surgery, or in a method for coating the above-mentioned material with the biomedical implant according to the present invention.

What is claimed is:

1. An organic/inorganic hybrid-porous biodegradable polymer scaffold, comprising:
   basic ceramic nanoparticles, an animal tissue or cell-derived bioactive first extracellular matrix material and a biodegradable polymer, and in which inner walls of pores are coated with a second extracellular matrix material.

2. The scaffold of claim 1, wherein the second extracellular matrix material is one or more selected from the group consisting of collagen, gelatin, elastin, silk, keratin, fibrinogen, hyaluronic acid, alginate, dextran, chondroitin sulfate, heparan sulfate, keratan sulfate, dextran sulfate, a protein based on an extracellular matrix including fibronectin, laminin, polysaccharides and a glycoprotein group.

3. The scaffold of claim 1, wherein the second extracellular matrix material is an extracellular matrix in which one or more selected from the group consisting of fibroblast, vascular endothelial cells, epithelial cells, cartilage cells, osteoblasts, smooth muscle cells, cardiomyocyte, liver cells, nerve cells, intervertebral disc cells, vascular endothelial cells, vascular endothelial progenitor cells, renal progenitor cells, pancreatic progenitor cells, neural progenitor cells, cardiac progenitor cells, adipose-derived stem cells, bone marrow-derived stem cells, mesenchymal stem cells, induced pluripotent stem cells and embryonic stem cells are decellularized.

4. The scaffold of claim 1, wherein the basic ceramic nanoparticles are one or more types of metal particles selected from alkali metals and alkali earth metals, or one or more types of particles selected from the group consisting of a hydroxide of an alkali metal, an oxide of an alkali metal, a hydroxide of an alkali earth metal and an oxide of an alkali earth metal.

5. The scaffold of claim 4, wherein the alkali metal or alkali earth metal is lithium (Li), beryllium (Be), sodium (Na), magnesium (Mg), potassium (K), calcium (Ca), rubidium (Rb), strontium (Sr), barium (Ba), cesium (Cs), francium (Fr) or radium (Ra).

6. The scaffold of claim 4, wherein the oxide of an alkali metal or an alkali earth metal, the hydroxide of an alkali metal or an alkali earth metal or the compound containing an alkali metal is one or more selected from the group consisting of lithium hydroxide, beryllium hydroxide, sodium hydroxide, magnesium hydroxide, potassium hydroxide, calcium hydroxide, rubidium hydroxide, strontium hydroxide, barium hydroxide, cesium hydroxide, francium hydroxide, radium hydroxide, magnesium oxide, sodium oxide, lithium oxide, manganese oxide, potassium oxide, calcium oxide, barium oxide, cesium oxide, radium oxide, magnesium sulfoxide, magnesium chloride, magnesium carbonate, magnesium bromide, magnesium stearate, magnesium perchlorate, magnesium citrate, magnesium phosphate, magnesium nitrate, magnesium nitride, magnesium iodide, magnesium acetate, magnesium ethoxide, magnesium fluoride, magnesium hydride, manganese monoperoxyphthalate, boron magnesium hydroxide, magnesium silicide, magnesium boride, magnesium aluminate, magnesium methylate, magnesium methalocyanin, magnesium salicylate, magnesium hexafluorosilicate, struvite, huntite, whitlockite, bredigite, dolomite, calcium carbonate, fluorspar, tricalcium phosphate and hydroxyapatite.

7. The scaffold of claim 1, wherein the basic ceramic nanoparticles are surface-modified with one or more fatty acids selected from the group consisting of caprylic acid, capric acid, lauric acid, myristoleic acid, palmitoleic acid, sapienic acid, oleic acid, elaidic acid, vaccenic acid, linoleic acid, ricinoleic acid, linoelaidic acid, α-linoleic acid, arachidonic acid, eicosapentaenoic acid, erucic acid, palmitate, stearic acid, DHA, octadecanoic acid, coconut oil, palm oil, cotton seed oil, wheat germ oil, bean oil, olive oil, corn oil, sunflower oil, safflower oil, hampseed oil and canola oil.

8. The scaffold of claim 1, wherein the basic ceramic nanoparticles are surface-modified with one or more polymer selected from the group consisting of L-lactide, D-lactide, D,L-lactide, glycolide, caprolactone, dioxanone, trimethylene carbonate, hydroxyalkanoate, peptide, cyanoacrylate, lactic acid, glycolic acid, hydroxycaproic acid, maleic acid, phosphazene, amino acid, hydroxybutyric acid, sebacic acid, hydroxyethoxyacetic acid and trimethylene glycol, which are one or more polymers selected from the group consisting of poly-L-lactide, poly-D-lactide, poly-D,L-lactide, polyglycolide, polycaprolactone, poly-L-lactide-co-glycolide, poly-D-lactide-co-glycolide, poly-D,L-lactide-co-glycolide, poly-L-lactide-co-caprolactone, poly-D-lactide-co-caprolactone, poly-D,L-lactide-co-caprolactone, poly(glycolide-co-caprolactone), polydioxanone, polytrimethylene carbonate, poly(glycolide-co-dioxanone), polyamideester, polypeptide, polyorthoester, polymaleic acid, polyphosphazene, polyanhydride, polycebacicanhydride, polyhydroxyalkanoate, polyhydroxybutylate and polycyanoacrylate.

9. The scaffold of claim 1, wherein the biodegradable polymer is one or more selected from the group consisting of polylactide, polyglycolide, polycaprolactone, polylactide-co-glycolide, polylactide-co-caprolactone, poly(glycolide-co-caprolactone), polydioxanone, polytrimethylene carbonate, poly(glycolide-co-dioxanone), polyamideester, polypeptide, polyorthoester, polymaleic acid, polyanhydride, polycebacicanhydride, polyhydroxyalkanoate, polyhydroxybutylate and polycyanoacrylate.

10. The scaffold of claim 1, wherein the animal tissue or cell-derived bioactive first extracellular matrix material is one or more selected from the group consisting of a group having a fiber structure, an osteogenic differentiation and ossification-related group, a glucoseaminoglycan group and a proteoglycan group.

11. The scaffold of claim 1, wherein the size of the basic ceramic nanoparticle is 1 nm to 1 mm.

12. The scaffold of claim 1, which includes 1 to 99 parts by weight of the basic ceramic nanoparticles, 1 to 99 parts by weight of the animal tissue or cell-derived bioactive extracellular matrix material, and 1 to 99 parts by weight of the biodegradable polymer with respect to 100 parts by weight of the organic/inorganic hybrid-porous biodegradable polymer scaffold.

13. A method for preparing an organic/inorganic hybrid-porous biodegradable polymer scaffold, comprising:
   (a) preparing an organic/inorganic hybrid polymer solution by dissolving or suspending basic ceramic nanoparticles, an animal tissue or cell-derived bioactive first extracellular matrix material, a biodegradable polymer and a pore inducer in an organic solvent;
   (b) preparing a porous biodegradable polymer scaffold by lyophilizing an organic/inorganic hybrid polymer to remove the pore inducer; and (c) culturing and decellularizing cells on the porous biodegradable polymer scaffold to coat inner walls of pores with a second extracellular matrix material.

14. The method of claim 13, wherein the pore inducer is ice particles.

15. The method of claim 13, wherein the pore inducer includes a second extracellular matrix material and ice particles.

16. The method of claim 13, wherein the step (c) is for culturing cells while the porous biodegradable polymer scaffold is immersed in a cell culture medium, wherein the cell culture medium includes one or more selected from the group consisting of angiopoietin, a bone morphogenetic protein (BMP), a granulocyte colony stimulating factor (G-CSF), a granulocyte macrophage colony-stimulating factor (GM-CSF), an epidermal growth factor (EGF), ephrin, erythropoietin, a fibroblast growth factor (FGF), a hepatocyte growth factor (HGF), an insulin-like growth factor (IGF), a keratinocyte growth factor (KGF), a nerve growth factor (NGF), a placental growth factor (PGF), a platelet-derived growth factor (PDGF), a transforming growth factor (TGF), a tumor necrosis factor-alpha (TNF-α) and a vascular endothelial growth factor (VEGF).

17. A method for preparing an organic/inorganic hybrid-porous biodegradable polymer scaffold, comprising:
(a) preparing an organic/inorganic hybrid polymer solution by dissolving or suspending a pore inducer including basic ceramic nanoparticles, an animal tissue or cell-derived bioactive first extracellular matrix material, a biodegradable polymer and a second extracellular matrix material in an organic solvent; and
(b) lyophilizing the organic/inorganic hybrid polymer solution to remove the pore inducer and coat inner walls of pores with the second extracellular matrix material.

* * * * *